(12) United States Patent
Holmström

(10) Patent No.: US 8,135,455 B2
(45) Date of Patent: Mar. 13, 2012

(54) SYSTEM AND METHOD FOR MONITORING SYNCHRONY BETWEEN CHAMBERS OF A HEART BY VOLUME MEASUREMENTS AND ANALYSIS

(75) Inventor: Nils Holmström, Järfalla (SE)

(73) Assignee: St. Jude Medical AB, Jarfalla (SE)

( * ) Notice: Subject to any disclaimer, the term of this patent is extended or adjusted under 35 U.S.C. 154(b) by 931 days.

(21) Appl. No.: 11/916,463

(22) PCT Filed: Jun. 16, 2005

(86) PCT No.: PCT/SE2005/000942
§ 371 (c)(1),
(2), (4) Date: Jun. 25, 2008

(87) PCT Pub. No.: WO2006/135290
PCT Pub. Date: Dec. 21, 2006

(65) Prior Publication Data
US 2009/0281438 A1    Nov. 12, 2009

(51) Int. Cl.
*A61B 5/04*    (2006.01)
(52) U.S. Cl. ....................................................... 600/509
(58) Field of Classification Search .................. 600/509; 607/115–117
See application file for complete search history.

(56) References Cited

U.S. PATENT DOCUMENTS

| | | | | |
|---|---|---|---|---|
| 5,792,195 A | * | 8/1998 | Carlson et al. | 607/17 |
| 7,283,783 B2 | * | 10/2007 | Larsson et al. | 455/3.01 |
| 2004/0172077 A1 | * | 9/2004 | Chinchoy | 607/17 |

* cited by examiner

*Primary Examiner* — Carl H Layno
*Assistant Examiner* — Paula J Stice
(74) *Attorney, Agent, or Firm* — Schiff Hardin LLP

(57) ABSTRACT

An implantable heart monitoring system includes a housing configured for implantation in a subject, at least one sensor member implanted relative to the heart of the subject to detect an electrical signal related to cardiac activity of the heart, a control circuit in the housing, and a memory accessible by the control circuit. The control circuit, from said electrical signal, derives a first value related to the volume of a first part of the heart and derives a second value related to the volume of a second part of the heart, and monitors variation of said first value over time in at least a substantial portion of a heart cycle, and monitors variation of said second value over time in said substantial portion of said heart cycle, and stores in the memory information representing the monitoring of said first and second values that represents a relationship between the first and second values in the substantial portion of the heart cycle and variation of the relationship in the substantial portion of the heart cycle.

20 Claims, 4 Drawing Sheets

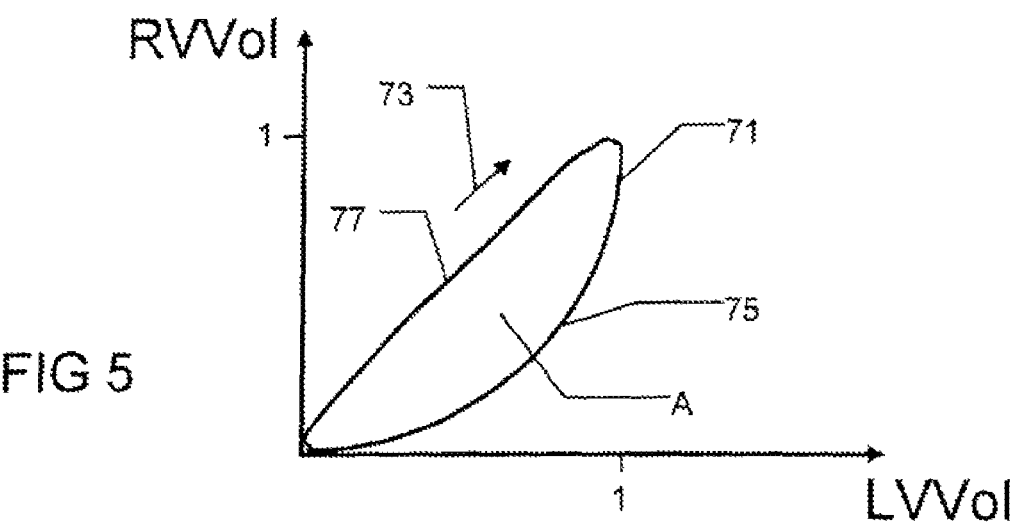
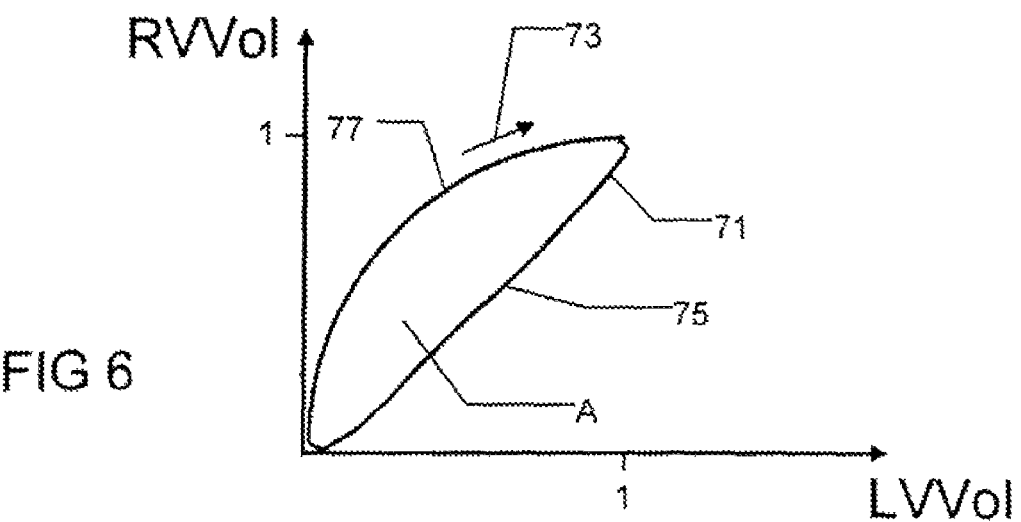

SYSTEM AND METHOD FOR MONITORING SYNCHRONY BETWEEN CHAMBERS OF A HEART BY VOLUME MEASUREMENTS AND ANALYSIS

BACKGROUND OF THE INVENTION

1. Field of the Invention

The present invention relates to an implantable heart monitoring device of the type having a control circuit and a memory connected to the control circuit. The control circuit is in communication with one or more sensor members suitable to be positioned in or at the heart of a living being. The control circuit is also arranged to at least enable the following: based on signals, received from the one or more sensor members, derive a first value, related to the volume of a first part of the heart, and, based on signals, received from the one or more sensor members, derive a second value, related to the volume of a second part of the heart. The invention also relates to a system including such a device and to the use of the system. The device may be used to monitor the performance of a heart of a human or animal being, and also to deliver stimulation pulses to the heart.

2. Description of the Prior Art

Several different devices for monitoring the performance of a heart are known. Often these devices are also able to deliver stimulation pulses to the heart. The devices are often able to sense the electrical activity of the heart. It is also known to sense an impedance value measured between different electrodes positioned in the heart. It is also known to sense other physiological parameters, such as pressure, oxygen level etc.

U.S. Pat. No. 6,070,100 describes that electrodes may be positioned in both the left and the right atrium as well as in or at the left and the right ventricles. The document describes the possibility of sensing the impedance between different electrodes. The sensed impedance values may be used to improve the cardiac output.

U.S. Pat. No. 5,720,768 describes different possible electrode positions in order to stimulate or sense the different chambers of the heart.

U.S. Pat. No. 5,154,171 describes the sensing of impedance values in order to control the pacing rate.

U.S. Pat. No. 6,604,002 describes different manners of using the proximal and distal electrodes of different leads in order to inject a current and to measure an impedance. The measured impedance value may be used in order to maximize the cardiac flow.

U.S. Pat. No. 6,556,866 describes bi-ventricular pacing. An impedance may be measured between electrodes on the right and the left sides of the heart. The variation of the impedance with time is detected. The detected impedance variation may be used in order to synchronize the contraction of the ventricles.

U.S. Pat. No. 6,280,389 describes a bi-ventricular pacer. Pressure is sensed in the right and left ventricles. A graph showing the relation between left ventricular pressure and right ventricular pressure during a heart beat is formed. This graph will form a loop. The heart performance is related to the area within this loop.

The variation in pressure between the two ventricles, as described in the above mentioned document U.S. Pat. No. 6,280,389, is not always the best measure for analyzing the performance of the heart and, consequently, not always the best basis for controlling the delivery of pacing pulses in order to optimize the performance of the heart. Furthermore, it can be difficult to measure the pressure, in particular in the left ventricle.

SUMMARY OF THE INVENTION

An object of the invention is to provide an implantable heart monitoring device with improved capacity for monitoring the heart function. A further object is to provide such a device, the operation of which can be controlled in an accurate manner based on the monitored heart function. Further objects and advantages will become clear from the following description and claims.

The above objects are achieved by an implantable heart monitoring device having:
a control circuit,
a memory connected to the control circuit,
the control circuit being adapted to stand in communication with one or more sensor members suitable to be positioned in or at the heart of a living being, the control circuit also being arranged to at least enable the following:
based on signals, received from the one or more sensor members, derive a first value, related to the volume of a first part of the heart, and monitor how this first value varies with time over at least a substantial portion of a heart cycle,
based on signals, received from the one or more sensor members, derive a second value, related to the volume of a second part of the heart and monitor how this second value varies with time over at least said substantial portion of a heart cycle,
store in the memory information of the monitored first and second values over the at least substantial portion of a heart cycle, wherein the information is sufficient in order to be able to derive a relationship between the first and second values over at least the substantial portion of a heart cycle, including information of how the relationship varies over the substantial portion of a heart cycle.

In this device, information is thus stored in the memory. This information includes a relationship between the first and second values including information of how the relationship varies. The mentioned relationship can thus represent how the volumes of the mentioned first and second parts of the heart vary. The variation of these volumes, and in particular how these volumes vary in relation to each other, has been found to be a highly relevant indication of how well the heart works. The invention can be used for different purposes. One particularly important use is for patients suffering from congestive heart failure or other severe cardiac diseases. As will be explained below, the device according to the invention can be used to improve the function of the heart of such patients.

It can be noted that the concept "heart cycle" is clear to those skilled in the art. Sometimes the expression "heart beat" is used with the same meaning as "heart cycle".

It should also be noted that the sensor members (and the electrode members described further below) are preferably arranged on leads adapted to be connected to the device. However, it is also feasible for the sensor members (electrode members) to communicate with the device in a wireless manner.

In an embodiment of the device according to the invention, the control circuit is arranged to enable the relationship to include information, if the one or more sensor members are appropriately arranged, of the difference and/or ratio between the volume, or a normalized value of the volume, of the first part of the heart, and the volume, or a normalized value of the volume, of the second part of the heart, as well as information concerning how this difference and/or ratio varies over said substantial portion of a heart cycle. As will be explained below, for example the ratio between the volumes, and how this ratio varies over a heart cycle, provides a very accurate picture of how well the heart works.

In a further embodiment of the device according to the invention, the control circuit is arranged so that, if the one or more sensor members are appropriately arranged, the first part is a first ventricle of the heart and the second part is the second ventricle of the heart. The invention is particularly useful for monitoring the volumes of the ventricles of the heart. The invention can thereby monitor whether the ventricles are well synchronized in their operation.

In a further embodiment of the device according to the invention, the control circuit is arranged to be able to monitor the first and second values over a whole, or at least substantially a whole, heart cycle. By monitoring the values during a whole heart cycle a good picture of how well the heart works is obtained. The expression "substantially a whole heart cycle" can for example mean at least 80% of a heart cycle.

In a further embodiment of the device according to the invention, the control circuit monitors the first and second values such that, if the variation of said first and second values over the whole, or at least substantially whole, heart cycle were to be represented in a Cartesian coordinate system, the first axis representing the first value and the second axis representing the second value, then this representation forms a complete, or at least substantially complete, loop in the Cartesian coordinate system. Consequently, preferably the loop is stored in the memory. As will be explained in the description below, the loop provides important information concerning the function of the heart.

In a further embodiment of the device according to the invention, the control circuit calculates a value related to the area within the loop. The area within the loop is related to the function of the heart. For example, a small such area can mean that the two ventricles are well synchronized.

In a further embodiment of the device according to the invention, the control circuit registers whether the loop, during the whole, or at least substantially whole, heart cycle is formed in a clockwise or counter-clockwise direction. The direction is which the loop is formed indicates, for example, which of the ventricles contracts first.

In a further embodiment of the device according to the invention, the control circuit monitors the first and second values at least over the whole, or a substantial portion of, the diastolic portion of the heart cycle and the control circuit enables the relationship to include information, if the one or more sensor members are appropriately arranged, of the ratio between the volume, or a normalized value of the volume, of the first part of the heart and, on the other hand, the volume, or a normalized value of the volume, of the second part of the heart, as well as information concerning how this ratio varies over the whole, or substantial portion of, the diastolic portion of the heart cycle, and the control circuit registers how much this ratio varies over the whole, or substantial portion of, the diastolic portion of the heart cycle. For some patients it may be important that, for example, the ventricles are very well synchronized during the diastolic portion of the heart cycle. In this case, the mentioned ratio should vary as little as possible. Since the control circuit registers how much this ratio varies, information is obtained as to how well synchronized the ventricles are during this diastolic portion.

In a further embodiment of the device according to the invention, the control circuit monitors the first and second values at least over the whole, or a substantial portion of, the systolic portion of the heart cycle and the control circuit enables the relationship to include information, if the one or more sensor members are appropriately arranged, of the ratio between the volume, or a normalized value of the volume, of the first part of the heart, and the volume, or a normalized value of the volume, of the second part of the heart, as well as information concerning how this ratio varies over said whole, or substantial portion of, the systolic portion of the heart cycle, and the control circuit registers how much this ratio varies over the whole, or substantial portion of, the systolic portion of the heart cycle. For some patients it may be particularly important that, for example, the ventricles are very well synchronized during the systolic portion of the heart cycle. This embodiment of the invention thus provides relevant information concerning such synchronization.

In a further embodiment of the device according to the invention, the control circuit is able to monitor the first and second values over at least a substantial portion of a number of heart cycles and to store the monitored values in said memory so as to provide information which makes it possible to determine how the relationship varies between different heart cycles. An important aspect of the invention is to monitor how the mentioned relationship varies between different heart cycles. It is thereby possible to see if the heart condition improves or gets worse.

In a further embodiment of the device according to the invention, the control circuit is in communication with a number of the sensor members and derives impedance values of the impedance between different such sensor members, the first and second values representing, or being derived from, such impedance values. Such impedance values can thus be used for obtaining information concerning the volumes of the mentioned first and second parts of the heart.

It should be noted that impedance measurement is one manner of deriving information of the volumes of the different chambers of the heart. However, the invention is in no way limited to the use of impedance measurement in order to determine these volumes. Any other manner of determining the volume of the heart chambers can be used. It is, for example, possible to determine the volume by emitting, which the help of an emitter, a sound wave in the heart and to sense the time it takes for this sound wave to be reflected back, by different walls of the heart, to a sensor, which may be positioned close to the emitter. Also by such measurement an estimation of the volume of heart chambers can be obtained.

In a further embodiment of the device according to the invention, the device also includes circuitry for delivering pacing pulses to one or more electrode surfaces, in communication with the device and suitable to be positioned in or at the heart of a living being, such that pacing pulses can be delivered to the heart, and the control circuit controls the delivery of the pacing pulses and to enable at least one pacing parameter to be varied. The device can thus be used, not only to monitor the function of the heart, but also to deliver pacing pulses in order to improve the heart function.

In a further embodiment of the device according to the invention, the control circuit is arranged to enable the following:
 vary the pacing parameter,
 register how the aforementioned relationship is changed when the pacing parameter is varied,
 determine at least one appropriate pacing parameter such that the relationship fulfils a predetermined criteria.

A pacing parameter can thus be selected on the basis of the monitored relationship. In this manner, pacing pulses can be delivered in a manner that improves the function of the heart.

In a further embodiment of the device according to the invention, the control circuit causes the pacing parameter to be first changed, when varying the pacing parameter, dependent on whether the loop is formed in a clockwise or counterclockwise direction. The direction in which the loop is formed can thus be used to determine, for example, whether a certain pacing parameter ought to be increased or decreased.

In a further embodiment of the device according to the invention, the control circuit includes an indicator component that indicates when a patient in whom the device is implanted is likely to be at rest, and the control circuit causes the determination, based on the variation of the pacing parameter, to be carried out when the indicator component indicates that the patient is likely to be at rest. Since the activity of the patient is likely to influence the heart function, it is appropriate to set the pacing parameter (or parameters) when the patient is at rest.

The mentioned indicator component can be an activity sensor. However, also other means are possible. The indicator for component may, for example, be formed by a clock. The clock can thus indicate, for example, that it is in the middle of the night, and that the patient, consequently, is likely to be at rest.

In a further embodiment of the device according to the invention, the control circuit causes the predetermined criteria to include a requirement to minimize said area or at least a requirement involving the fact that the area shall be small. A small area can, for example, mean that the ventricles are well synchronized. Consequently, the requirement that the area shall be small (or minimized) can be used to select an appropriate pacing parameter.

A further embodiment of the device according to the invention, the control circuit causes the predetermined criteria to include a requirement to minimize the variation of said ratio over the whole, or substantial portion of, the diastolic portion of the heart cycle, or at least a requirement involving the fact that the variation of the ratio over said whole, or substantial portion of, the diastolic portion of the heart cycle shall be small. As mentioned above, for some patients it is important that for example the ventricles are well synchronized during the diastolic portion of the heart cycle. Consequently, the variation of the mentioned ratio during the diastolic portion of the heart cycle can be used to find an appropriate pacing parameter.

A further embodiment of the device according to the invention, the control circuit causes the predetermined criteria to include a requirement to minimize the variation of said ratio over said whole, or substantial portion of, the systolic portion of the heart cycle, or at least a requirement involving the fact that the variation of the ratio over the whole, or substantial portion of, the systolic portion of the heart cycle shall be small. As also mentioned above, for some patients it is important that, for example, the ventricles are well synchronized during the systolic portion of the heart cycle. Consequently, the variation of the mentioned ratio during the systolic portion of the heart cycle can be used to select a suitable pacing parameter.

In a further embodiment of the device according to the invention, the device operates with a VV-interval, the VV-interval being the time, within one heart cycle, between a sensed and/or paced event in a first ventricle and a sensed and/or paced event in the second ventricle, and the pacing parameter is this VV-interval. For some patients it is beneficial to use a so-called bi-ventricular pacer. Such a pacer operates with a VV-interval. The present invention is particularly applicable to be used in such a pacer. By selecting an appropriate VV-interval the synchrony of the ventricles can be improved. The VV-interval is usually less than 50 ms long.

In a further embodiment of the device according to the invention, the device operates with an AV-interval, the AV-interval is the time, within one heart cycle, between a sensed and/or paced event in an atrium and a sensed and/or paced event in a ventricle, and the pacing parameter is this AV-interval. The invention can also be used to set for example an AV-interval. Of course, the invention can be used both to set a suitable VV-interval and an AV-interval.

Another aspect of the invention relates to an implantable heart monitoring system. This system has a heart monitoring device according to any of the preceding embodiments, and the one or more sensor members, and the control circuit is communicates with the one or more sensor members.

According to an embodiment of the system according to the invention, the system has one or more electrode surfaces, as defined above, which electrode surfaces may be identical or not with the one or more sensor members.

With a system according to the invention, advantages corresponding to those described above are obtained.

Another aspect of the invention relates to the use of a system according to the invention. According to this use, the system is implanted in a living being and the one or more sensor members are positioned in or at the heart of said living being.

According to one manner of using the system, also the one or more electrode surfaces are positioned in or at the heart of the living being.

According to a further manner of using the system, the system is used such that first part is a first ventricle of the heart and the second part is the second ventricle of the heart.

According to a further manner of using the system, the system is used to determine at least one appropriate pacing parameter and then operate the device in accordance with the determined pacing parameter.

When the system is actually used in a patient, the above described advantages of the device according to the invention are achieved in an actual patient.

BRIEF DESCRIPTION OF THE DRAWINGS

FIGS. 2 through 6 respectively schematically illustrate different examples of the relationship between right ventricular volume and left ventricular volume during a heart cycle, represented in a Cartesian coordinate system, as used in accordance with the present invention.

DESCRIPTION OF THE PROFFERED EMBODIMENTS

Figure 1:
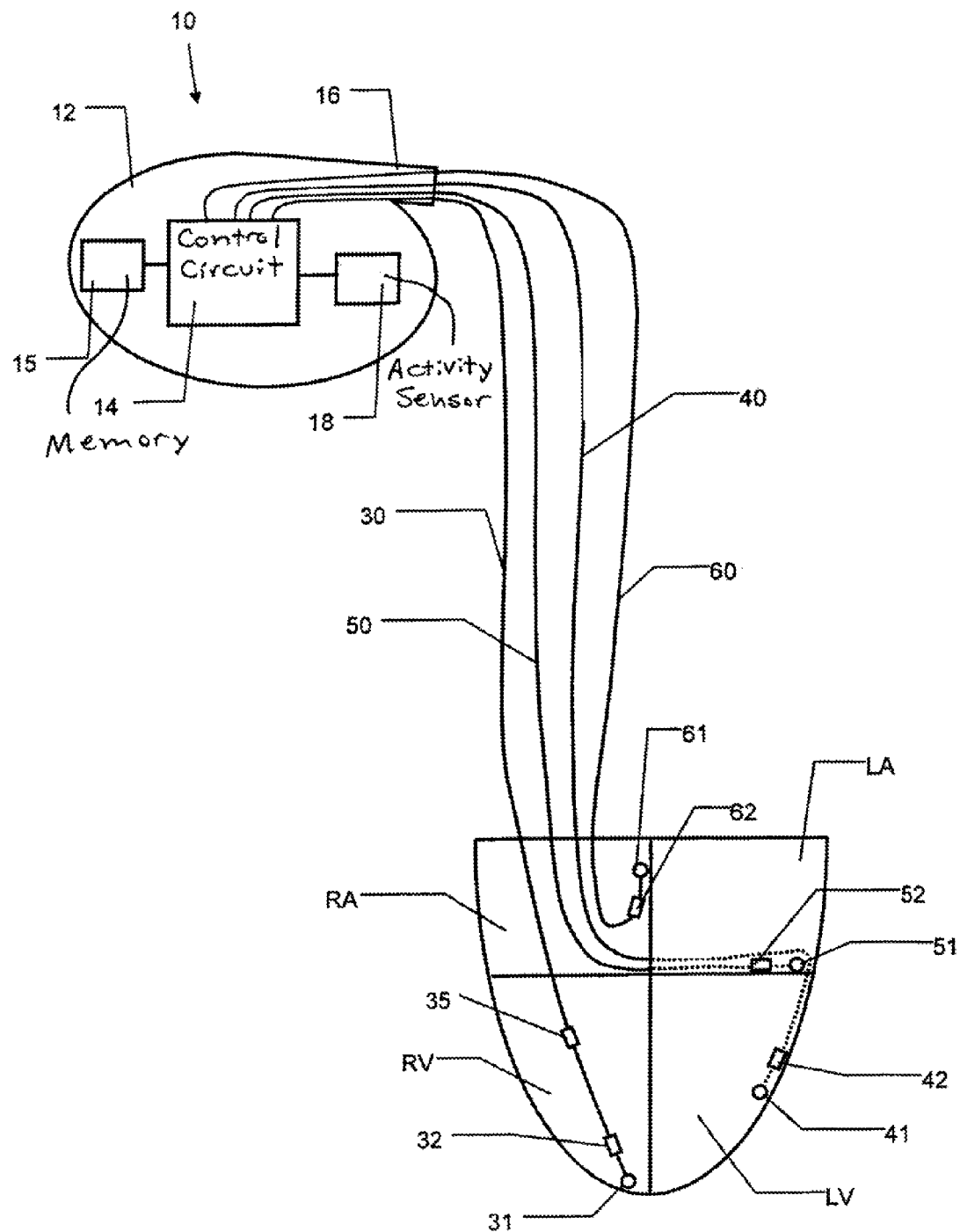
FIG. 1 schematically illustrates a heart monitoring system, formed by a heart monitoring device connected to leads with sensor members/electrode members positioned in a heart, in accordance with the present invention.

An embodiment of the invention will now first be described with reference to FIG. 1. FIG. 1 thus schematically shows a heart monitoring device 10. The device 10 is connected to a plurality of leads 30, 40, 50, 60. In this case there are thus four leads 30, 40, 50, 60. However, the number of leads may vary. The leads 30, 40, 50, 60 are connected to the device 10 at a connector portion 16 of the device 10. The device 10 has a housing 12. Inside the housing a control circuit 14 is arranged. The control circuit 14 is thus connected to the leads 30, 40, 50, 60. The device 10 may also be provided with an activity sensor 18. Such an activity sensor 18 may be used to sense the activity level of a living being into which the device is implanted. Such an activity sensor 18 may be constructed in different manners known to the person skilled in the art. The device 10 is constructed such that it is suited to be implanted in a living being, i.e. into a human or animal being. The device also has at least one memory 15 connected to the control circuit 14.

A number of sensor members 31, 32, 35; 41, 42; 51, 52; 61, 62 are provided on the leads 30, 40, 50, 60. The sensor members are connected to the control circuit 14 with the help of the leads 30, 40, 50, 60. The leads thus include electric conductors (not shown) which may conduct signals from the different sensor members to the control circuit. The device 10 together with the leads 30, 40, 50, 60 and the sensor members 31, 32, 35, 41, 42, 51, 52, 61, 62 form a heart monitoring system according to the invention. The sensor members 31, 32, 35, 41, 42, 51, 52, 61, 62 may be used to derive a value related to the volume of different parts of a heart. It should be noted that in the shown embodiment, each lead is provided with at least two such sensor members 31, 32 etc. The lead may thus be said to be a bi-polar lead. However, it is also possible that each lead only comprises one such sensor member i.e. also unipolar leads are possible. The different sensor members 31, 32, 35, 41, 42, 51, 52, 61, 62 may also, according to one embodiment of the invention, be used to deliver stimulation pulses to a heart. The sensor members do in this case also constitute electrode surfaces adapted to deliver stimulation pulses to the heart, in order to pace the heart.

FIG. 1 also schematically shows a heart with a right atrium RA, a right ventricle RV, a left atrium LA and a left ventricle LV.

In the illustrated embodiment, the sensor members 31, 32 are positioned in the heart near the apex of the right ventricle RV. The sensor member 35 is arranged further up in the right ventricle RV.

The lead 40 is positioned such that it may have been introduced through the right atrium RA, via the coronary sinus into, for example, the posterior, lateral or anterior vein of the left ventricle LV. The electrodes 41, 42 are thus positioned in for example one of said veins of the left ventricle LV. In the shown embodiment, the third lead 50 is introduced such that the electrodes 51, 52 are positioned in the coronary sinus or the great cardiac vein. The fourth lead 60 is introduced such that the electrodes 61, 62 are positioned in the right atrium RA. Other positions of the different sensing members 31, 32, 35, 41, 42, 51, 52, 61, 62 are also possible.

By sensing the impedance between suitable sensor members 31, 32, 35, 41, 42, 51, 52, 61, 62, in response to an injected current, a value related to the volume (of blood) of different parts of the heart can be obtained. How this is done is explained in some of the above disclosed documents concerning impedance measurement.

The control circuit 14 is arranged such that, based on signals, received from said one or more sensor members 31, 32, 35, 41, 42, 51, 52, 61, 62, it may derive a first value related to the volume of a first part RV of the heart. This can be done by sensing an impedance value Z between suitable sensor members. For example, the impedance Z between the sensor members 31 and 35, indicates the volume of blood in the right ventricle RV. The sensor member 35 is in addition to the two sensor members 31 and 32 which are normally present in a bi-polar lead. The sensor member 35 is arranged in order to derive an impedance value that very accurately can represent the volume of blood in the right ventricle RV. However, it is also possible to derive an impedance value related to the volume of blood in the right ventricle RV without using the sensor member 35, for example by measuring the impedance between the sensor members 31 and 32.

The control circuit 14 is also arranged such that, based on signals, received from said one or more sensor members 31, 32, 35, 41, 42, 51, 52, 61, 62, it may derive a second value related to the volume of a second part LV of the heart. This can be done by sensing an impedance value Z between suitable sensor members. For example, the impedance Z between the sensor members 31 and 42, indicates the volume of blood in the left ventricle LV.

The control circuit 14 is arranged to monitor how the first and second values vary with time over at least a substantial portion of a heart cycle.

The control circuit 14 is also arranged to store in the memory 15 information of the first and second values over the at least substantial portion of a heart cycle. This information includes a relationship between the first and second values over at least the substantial portion of a heart cycle, including information of how the relationship varies over the substantial portion of a heart cycle. Preferably, the first and second values are monitored over a whole heart cycle. Moreover, preferably, the first and second values are monitored over several heart cycles, which makes it possible to determine how the relationship varies between different heart cycles.

The control circuit 14 is also arranged to control the delivery of pacing pulses to the heart, i.e. pulses that electrically stimulate the heart. Such pacing pulses can be delivered via electrode surfaces. The mentioned sensor surfaces 31, 32, 41, 42, 51, 52, 61, 62 can also be used as electrode surfaces in order to stimulate the heart. Since this is well known to those skilled in the art, this matter need not be described further herein.

Furthermore, the device 10 according to the invention may be arranged to include features normal for such heart monitoring or pacing devices. For example, the control circuit 14 may be arranged to sense the electrical activity of the heart, to inhibit the delivery of pacing pulses, to provide back-up pulses if necessary, to vary the pacing rate, to automatically adjust pacing parameters, etc, as is well known to a person skilled in the art.

The function of the device 10 will now be more closely described in connection with FIG. 2-6. In the following example, the mentioned first part of the heart is the right ventricle RV and the mentioned second part of the heart is the left ventricle LV.

Figure 2:
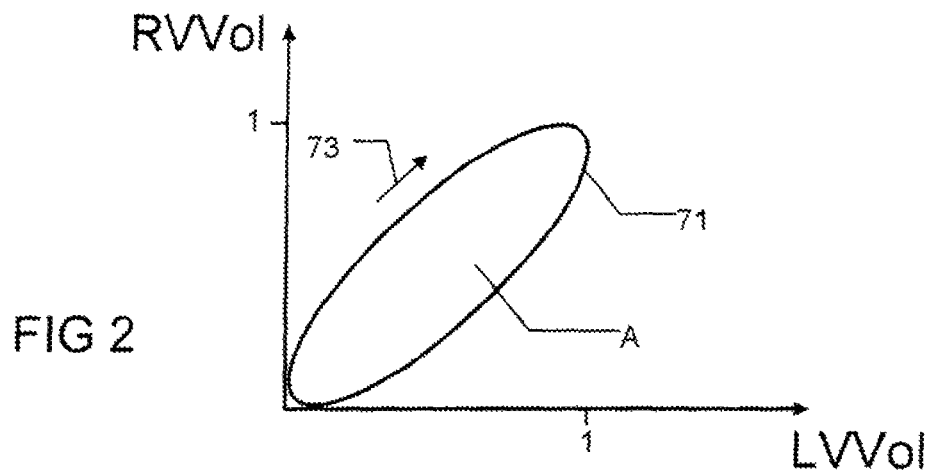

FIG. 2 illustrates schematically the relationship between right ventricular volume RVVol and left ventricular volume LVVol during a heart cycle. FIG. 2 does in fact illustrate normalized values of the volume, where the volume for the respective ventricle varies between 0 and 1. Zero thus represents the minimum volume during the heart cycle and one the maximum volume during the heart cycle in question. The relationship illustrated in FIG. 2 shows how the normalized values of the volumes of the two ventricles vary during the heart cycle. The variation of these volumes is represented in FIG. 2 by a loop 71. Each point on this loop 71 thus represents the two (normalized) volumes at a particular moment in time during the heart cycle. The arrow 73 indicates in which direction the loop 71 is formed during the heart cycle. The direction of the arrow 73 in FIG. 2 indicates that the volume of the right ventricle RV increases before the volume of the left ventricle LV during the portion of the heart cycle where these volumes increase, i.e. during the diastolic phase. If the loop 71 is formed in the clockwise direction, as indicated by the arrow 73 in FIG. 2, then the right ventricle RV can be said to be ahead of the left ventricle LV.

Since each point on the loop 71 illustrates the normalized volumes of the two ventricles, the loop 71 includes information concerning the ratio between RVVol and LVVol.

"A" represents the area within the loop 71. The control circuit 14 is arranged to calculate a value related to this area A.

This area A is a measure of how well synchronized the two ventricles RV and LV are. A small area A means that two ventricles RV and LV are well synchronized.

FIGS. 3-6 illustrate other loops 71 similar to the loop 71 of FIG. 2.

Figure 3:
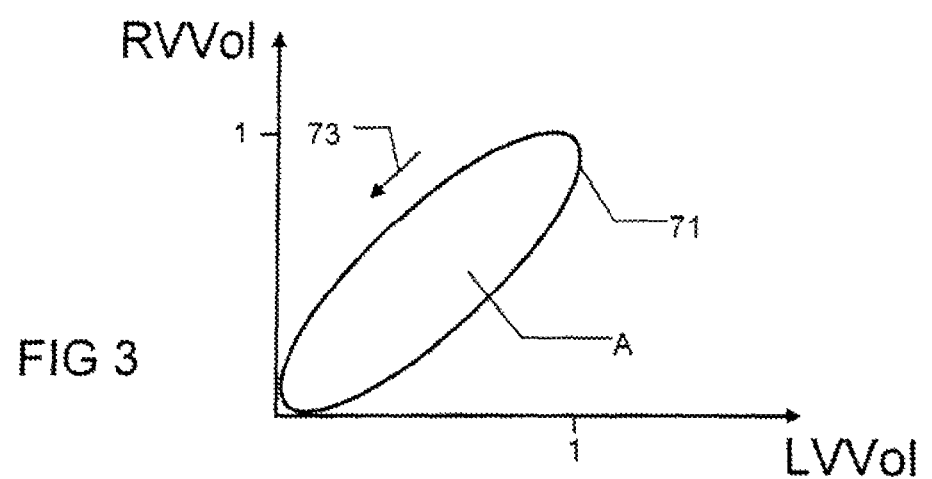

FIG. 3 shows a loop 71 that is very similar in shape to the loop 71 of FIG. 2. However, the arrow 73 in FIG. 3 illustrates that the loop 71 in this figure is formed in the counter-clockwise direction. This means that in this case, the left ventricle LV is ahead of the right ventricle RV.

Figure 4:
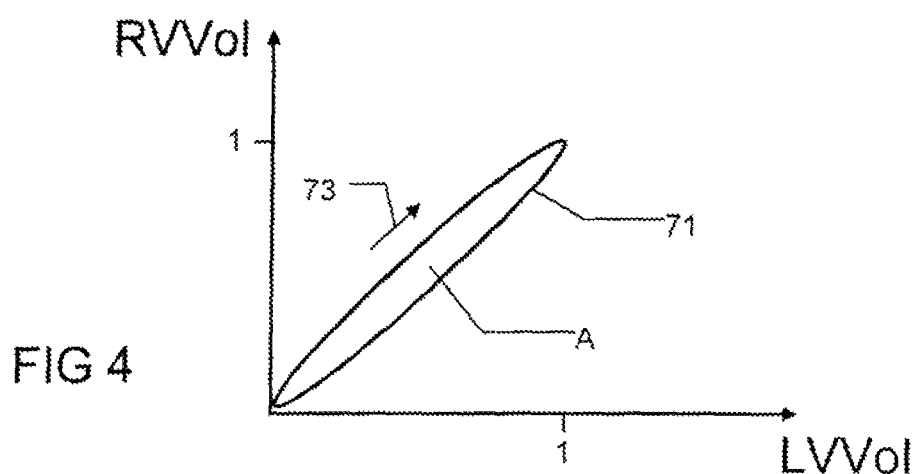

FIG. 4 illustrates a loop 71 with a substantially smaller area A than the loop 71 in FIGS. 2 and 3. This means that in the case illustrated in FIG. 4, the two ventricles RV and LV are much better synchronized than the ventricles RV and LV in FIGS. 2 and 3.

FIG. 5 illustrates a similar loop 71 to the loops 71 shown in-FIG. 2-4. However, in FIG. 5 it can be seen that the part 77 of the loop 71 is more straight than the part 75 of the loop 71. The part 75 represents the systolic portion of the heart cycle. The part 77 represents the diastolic portion of the heart cycle. The portion 77 is almost straight, while the portion 75 is more curved. This means that in the case illustrated in FIG. 5, the ventricles RV and LV are very well synchronized during the diastolic portion 77 but less well synchronized during the systolic portion 75. The control circuit 14 can be arranged to monitor and register how much the ratio, in normalized values, between the right ventricular volume RVVol and the left ventricular volume LVVol varies during the diastolic portion of the heart cycle. Since the portion 77 of the loop 71 is substantially straight in FIG. 5, this means that the ratio between the normalized right ventricle volume and the normalized left ventricle volume varies very little or not at all during the diastolic phase. The control circuit 14 can be arranged to register how much the ratio between the volumes (or the normalized volumes) of the right ventricle RV and the left ventricle LV varies during the diastolic portion of the heart cycle. Any suitable measure of this variation may be used.

FIG. 6 illustrates a loop similar to one in FIG. 5. However, in the loop 71 of FIG. 6, the portion 75 is relatively straight while the portion 77 is less straight. In the case illustrated in FIG. 6 it is thus the case that the ventricles are very well synchronised during the systolic portion of the heart cycle but less synchronised during the diastolic phase of the heart cycle. The control circuit 14 can be arranged to monitor and to register how much the ratio between the volumes (or the normalised volumes) of the right ventricle RV and the left ventricle LV varies during the systolic portion of the heart cycle. Any suitable measure of this variation may be used.

Figure 7:
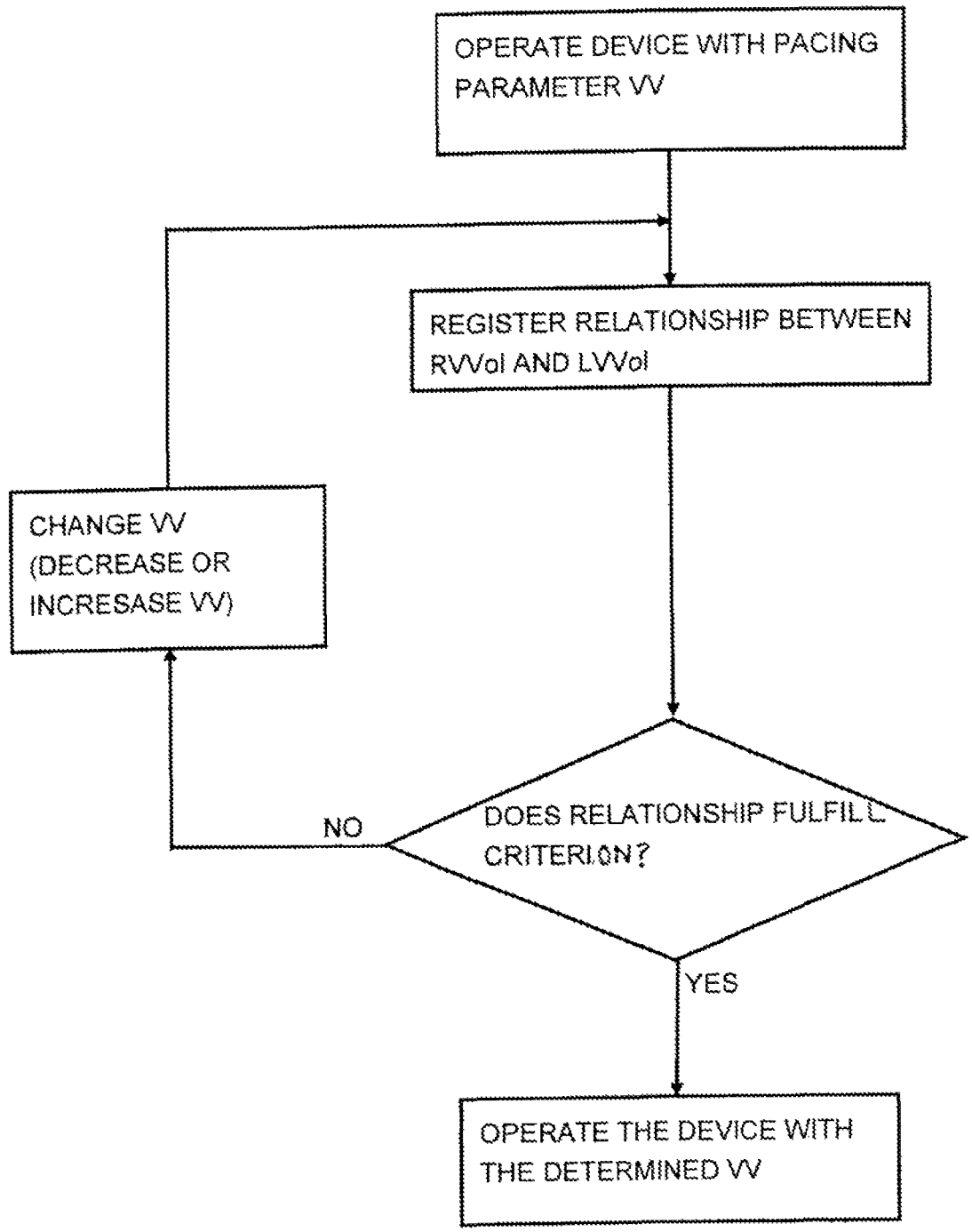
FIG. 7 is an exemplary flow chart describing operation of an embodiment of the inventive system and method.

FIG. 7 illustrates schematically a manner in which the device 10 according to the invention can operate. In the shown example, it is assumed that the device 10 is a bi-ventricular pacer that can deliver pacing pulses to both the ventricles RV and LV. It is also assumed that this device 10 operates with a VV-interval. The VV-interval is the time, within one heart cycle, between a sensed and/or paced event in a first ventricle (for example RV) and a sensed and/or paced event in the second ventricle (for example LV). The VV-interval thus constitutes a pacing parameter. The operation of the device 10 involves the fact that a pacing parameter is varied. It is registered how the mentioned relationship between the volumes is changed when the pacing parameter is varied. An appropriate pacing parameter is then determined such that the relationship fulfils a predetermined criteria. This can be done, for example, as illustrated in FIG. 7.

The device 10 first operates with a certain VV-interval. A relationship between RVVol and LVVol is registered. This can be done by registering a loop 71 of the kind shown in FIG. 2-6. This registration may involve the calculation of the area A within the loop 71. At the next step it is determined whether the relationship (for example the area A) fulfils a certain criteria. The criteria may, for example, be that the area A is smaller than a predetermined value. Another criteria may be that the area A is a minimum area that has been obtained by varying the pacing parameter VV. If the criteria is not fulfilled, then the VV-interval is changed. The direction in which the VV-interval is changed (i.e. whether the VV-interval is increased or decreased) can depend on whether the registered loop 71 is formed in a clockwise or counter-clockwise direction. For example, if the loop 71 is formed in a clockwise direction as illustrated in FIG. 2, this means that the right ventricle RV is ahead of the left ventricle LV. In this case, the VV-interval may first be changed in a direction such that the right ventricle RV is likely to be less ahead of the left ventricle LV than before. For example, if a positive VV-interval means that the right ventricle RV is paced before the left ventricle LV, then the VV-interval would be decreased in this case.

Thereafter the relationship between RVVol and LVVol is registered again. At the next step it is determined whether the relationship fulfils the criteria in question. This procedure continues until the criteria is fulfilled. If the criteria is fulfilled, then the device 10 is set to operate with the VV-interval determined by this procedure.

In the example illustrated in FIG. 7 it is the VV-interval that is determined. However, a similar procedure can be used also for other pacing parameters. For example, the AV-interval can be determined in a similar manner.

Furthermore, although in the above example the area A was used as the criteria in question, also other criterias may be used. For example, for some patients it may be particularly important that the ventricles are synchronized during the systolic portion of the heart cycle. In this case, the mentioned variation of the ratio in volumes between the ventricles during the systolic portion of the heart cycle may be used as a criteria. The criteria can thus be that this variation shall be smaller than a predetermined value or that the variation of the ratio should be minimized during the systolic portion of the heart cycle. For another patient, it may be particularly important that the ventricles are well synchronized during the diastolic portion of the heart cycle. Consequently, the criteria can in this case be that the variation of the ratio between the volumes of the ventricles shall be lower than a predetermined value or minimized during the diastolic phase.

Also other criterias are of course possible. It is for example possible to form a criteria that depends both on the area A and on the variation of said ratio between the volumes during the diastolic or the systolic portion of the heart cycle.

The procedure illustrated in FIG. 7 for determining a pacing parameter may be carried out at regular intervals. Preferably, the control circuit 14 includes means 18 arranged to indicate when the patient in whom the device is implanted is likely to be at rest. The procedure illustrated in FIG. 7 is suitably carried out when the patient is at rest, since otherwise it may be difficult to determine the pacing parameter in question accurately. The procedure according to FIG. 7 may thus be carried out for example when the person is asleep.

It should be noted that the pacing parameter in question (for example the VV-interval) can also be determined in other manners known to those skilled in the art. Once an appropriate VV-interval has been determined, it is possible to with the help of the device 10 according to the invention register the shape of the loop 71 when the device 10 operates with the set VV-interval. In this case, the registered form of the loop 71 can later be used to modify the VV-interval if necessary. In this case, a later registered loop 71 can be compared with the previously determined loop 71 and the criteria can be that the newly registered loop 71 shall be as similar as possible to the already registered loop 71.

The control circuit 14 can include a filter that filters out variations in the impedance measurement that depend on other factors than on the volume change during the heart cycle. Such other factors may be due to for example respiration and lung edema. Such factors usually show a slow variation (usually less than 1 Hz). Consequently, such slow variations may be filtered out when determining the volumes with the help of impedance measurement.

It should also be mentioned that this loop may in fact be registered as an average loop over several heart cycles, wherein the device is operated with the same VV-interval during the time this "average loop" is registered. The formation of such an "average loop" has the advantage that an individual deviation during a heart cycle from how the heart normally operates has less influence on the result.

As mentioned above, the invention also concerns a heart monitoring system. This system includes a heart monitoring device 10 as described above together with one or more sensor members 31, 32, 35, 41, 42, 51, 52, 61, 62, and one or more electrode surfaces (which can be the same as the sensor members) suitable for delivering pacing pulses to the heart.

The invention also concerns the use of such a system. According to this use, the system is actually implanted in a living being and one or more sensor members 31, 32, 35, 41, 42, 51, 52, 61, 62 are positioned in or at the heart of the living being. Also one or more electrode surfaces, which may be the same as the sensor members, are positioned in or at the heart of the living being in order to be able to deliver pacing pulses to the heart. The system is preferably be used to monitor the volumes of the right ventricle RV and the left ventricle LV of the heart. The system can be used to determine a pacing parameter, for example the VV-interval, and then to operate the device 10 in accordance with the determined pacing parameter.

Although modifications and changes may be suggested by those skilled in the art, it is the intention of the inventors to embody within the patent warranted heron all changes and modifications as reasonably and properly come within the scope of their contribution to the art.

I claim as my invention:

1. An implantable heart monitoring system comprising:
    a housing configured for implantation in a subject having a heart beating in successive heart cycles each having a diastolic portion and a systolic portion;
    at least one sensor member implanted relative to the heart of the subject to detect an electrical signal related to cardiac activity of the heart;
    a control circuit in said housing;
    a memory accessible by said control circuit; and
    said control circuit being configured to derive, from said electrical signal, a first value related to a volume of a first part of the heart and to derive a second value related to a volume of a second part of the heart, and to monitor variation of said first value over time in at least a substantial portion of heart cycle selected from said diastolic portion and said systolic portion, and by representing said first value along a first axis of a Cartesian coordinate system and representing said second value along a second axis of said Cartesian coordinate system, to form a substantially complete loop in the Cartesian coordinate system;
    said control unit being configured to determine from said loop, a volume of said first part of the heart or a normalized value thereof and to determine a volume of the second part of the heart or a normalized value thereof, and to determine a difference or a ratio between the volume of said first part of the heart or a normalized value thereof and the volume of the second part of the heart or a normalized value thereof, and to determine, from said difference or ratio, a degree of synchrony between said first part of the heart and said second part of the heart in said substantial portion of the heart cycle;
    and said control unit being configured to emit said indication of said degree of synchrony as an output signal from the control circuit and to store said indication of said degree of synchrony in a memory.

2. A system as claimed in claim 1 wherein said at least one sensor and said control circuit are configured to derive said first value as being related to the volume of a first ventricle, as said first part of the heart, and to derive said second value as a value related to the volume of a second ventricle, as said second part of the heart.

3. A system as claimed in claim 1 wherein said control circuit is configured to monitor said first and second value over at least substantially an entire heart cycle, as said substantial portion of the heart cycle.

4. A system as claimed in claim 3 wherein said control circuit is configured to identify, as directional information, whether said loop, during said substantially entire heart cycle, is formed in a clockwise direction or in a counterclockwise direction, and to also emit said directional information in electronic form and to store said directional information in said memory.

5. A system as claimed in claim 1 wherein said control circuit is configured to monitor said first and second values over respective substantial portions of a plurality of different heart cycles, and to store said first and second values in said memory for each of said substantial portions of said plurality of heart cycles to represent variation of said relationship between different heart cycles.

6. A system as claimed in claim 1 comprising a plurality of sensor members in communication with said control circuit, and wherein said control circuit is configured to derive, as each of said first and second values, an impedance value between different ones of said plurality of sensors.

7. A system as claimed in claim 1 comprising a pulse generator in said housing that emits pacing pulses, and a pacing pulse delivery system comprising at least one electrode surface configured to interact with cardiac tissue to deliver said pacing pulses thereto, and wherein said pulse generator is connected to said control circuit and said control circuit is configured to control emission of said pacing pulses by said pulse generator to by varying at least one pacing parameter of said pacing pulses dependent on said indication of said degree of synchrony.

8. A system as claimed in claim 7 wherein said at least one sensor also serves as said at least one electrode surface.

9. A system as claimed in claim 7 wherein said control circuit is configured to register if and how said indication of said degree of synchrony changes upon variation of said pacing parameter and sets said pacing parameter to a pacing parameter value that causes said degree of synchrony to satisfy a predetermined criterion.

10. A system as claimed in claim 9 comprising a further sensor that emits a further sensor signal to said control circuit from which said control circuit is configured to determine when the subject is likely to be at rest, and wherein said control circuit is configured to vary said at least one pacing parameter and to determine whether said relationship fulfills said predetermined criterion only when said control circuit determines that the subject is likely to be at rest.

11. A system as claimed in claim 9 wherein said control circuit is configured to use, as said predetermined criterion, that an area of said loop is small.

12. A system as claimed in claim 9 wherein said control circuit is configured to, from said first and second values, a ratio between a volume of the first part of the heart or a normalized value thereof, and a volume of the second part of the heart or a normalized value thereof, and to use, as said predetermined criterion, that variation of said ratio over said substantial portion of the heart cycle is small.

13. A system as claimed in claim 9 wherein said control circuit is configured to operate said pulse generator with a VV interval that is a time, within one heart cycle, between a sensed or paced event in a first ventricle of the heart and a sensed or paced event in a second ventricle of the heart, and wherein said control circuit is configured to set said VV interval as said pacing parameter.

14. A system as claimed in claim 9 wherein said control circuit is configured to operate said pulse generator with an AV interval that is a time, within one heart cycle, between a sensed or paced event in an atrium of the heart and a sensed or paced event in a ventricle of the heart, and wherein said control circuit is configured to set said AV interval as said pacing parameter.

15. A method for operating an implanted heart monitoring device, comprising the steps of:
   implanting at least one sensor member relative to a heart of a subject, the heart beating in successive heart cycles each having a diastolic portion and a systolic portion, and detecting an electrical signal related to cardiac activity of the heart with said at least one sensor member;
   in a processor supplied with said electrical signal, automatically electronically deriving a first value related to the volume of a first part of the heart and a second value related to the volume of a second part of the heart from said electrical signal;
   in said processor, representing said first value along a first axis of a Cartesian coordinate system and representing said second value along a second axis of said Cartesian coordinate system, to form a substantially complete loop in the Cartesian coordinate system;
   in said processor, from said loop, deriving a volume of said first part of the heart or a normalized value thereof, and deriving a volume of the second part of the heart or a normalized value thereof;
   in said processor, determine a difference or a ratio between the volume of the first part of the heart or a normalized value thereof and the volume of the second part of the heart or a normalized value thereof;
   in said processor, generate an indication of a synchrony between said first part of the heart and said second part of the part from said ratio or said difference, and emitting said indication of said degree of synchrony as an electrical output from the processor; and
   storing said indication of said degree of synchrony in a memory in communication with said processor.

16. A method as claimed in claim 15 comprising emitting pacing pulses and delivering the pacing pulses to the heart via a delivery system comprising at least one electrode surface configured to interact with cardiac tissue, and automatically electronically varying at least one pacing parameter of said pacing pulses dependent on said indication of said degree of synchrony.

17. A method as claimed in claim 16 wherein using said at least one sensor also as said at least one electrode surface.

18. A method as claimed in claim 16 comprising automatically electronically registering if and how said relationship changes upon variation of said pacing parameter, and setting said pacing parameter to a pacing parameter value that causes said indication of said degree of synchrony to satisfy a predetermined criterion.

19. A method as claimed in claim 18 comprising emitting said pacing pulses with a VV interval that is a time, within one heart cycle, between a sensed or paced event in a first ventricle of the heart and a sensed or paced event in a second ventricle of the heart, and setting said VV interval as said pacing parameter.

20. A method as claimed in claim 18 comprising emitting said pacing pulses with an AV interval that is a time, within one heart cycle, between a sensed or paced event in an atrium of the heart and a sensed or paced event in a ventricle of the heart, and setting said AV interval as said pacing parameter.

* * * * *